United States Patent [19]

Crosby

[11] Patent Number: 4,551,281
[45] Date of Patent: Nov. 5, 1985

[54] PROCESS FOR THE PREPARATION OF CYCLOPROPANE CARBOXYLIC ACID ESTERS

[75] Inventor: John Crosby, Manchester, England

[73] Assignee: Imperial Chemical Industries PLC, London, England

[21] Appl. No.: 644,230

[22] Filed: Aug. 27, 1984

Related U.S. Application Data

[63] Continuation of Ser. No. 262,640, May 11, 1981, abandoned, which is a continuation of Ser. No. 81,056, Oct. 2, 1979, abandoned.

[30] Foreign Application Priority Data

Oct. 31, 1978 [GB] United Kingdom ............... 42531/78

[51] Int. Cl.$^4$ ........................................... C07C 67/317
[52] U.S. Cl. ................. 260/465 D; 560/124
[58] Field of Search ................. 560/124; 260/465 D

[56] References Cited

U.S. PATENT DOCUMENTS

| | | | |
|---|---|---|---|
| 4,166,064 | 8/1979 | Kondo | 560/124 |
| 4,183,948 | 1/1980 | Huff | 424/305 |
| 4,243,677 | 1/1981 | Engel | 424/305 |
| 4,252,820 | 2/1981 | Lantzsch | 424/304 |
| 4,258,202 | 3/1981 | Piccardi | 560/124 |

FOREIGN PATENT DOCUMENTS

| | | | |
|---|---|---|---|
| 2547510 | 4/1976 | Fed. Rep. of Germany | 560/124 |
| 2621835 | 11/1976 | Fed. Rep. of Germany | 560/124 |
| 1520023 | 8/1978 | United Kingdom | 560/124 |
| 2000764 | 1/1979 | United Kingdom | 560/124 |

OTHER PUBLICATIONS

Fieser, "Reagents for Organic Synthesis," pp. 606–607 (1967); vol. 3, p. 183 (1972); vol. 5, p. 395 (1975); and vol. 7, p. 200 (1979).
House, "Modern Synthetic Reactions," 2nd Ed., pp. 473–474 (1972).
Survey of Organic Synthesis (Buehler & Pearson) (1970), pp. 75–78.
Synthetic Reagents, vol. I, Pizey (1974), pp. 18–21.

Primary Examiner—Michael L. Shippen
Attorney, Agent, or Firm—Cushman, Darby & Cushman

[57] ABSTRACT

3-(2'-chloro-3',3',3'-trifluoropropenyl)-2,2-dimethylcyclopropane-1-carboxylic acid esters are prepared by dehydrohalogenation of the corresponding 3-(2',2'-dichloro-3',3',3'-trifluoropropyl) compounds by reaction with an alkali metal carbonate in a polar aprotic solvent. The products are intermediates in the preparation of pyrethroid insecticides or are themselves insecticides.

7 Claims, No Drawings

PROCESS FOR THE PREPARATION OF CYCLOPROPANE CARBOXYLIC ACID ESTERS

This is a continuation of application Ser. No. 262,640, filed May 11, 1981, now abandoned, as a continuation of Ser. No. 81,056, filed Oct. 2, 1979, now abandoned.

This invention relates to a process for the preparation of certain cyclopropane carboxylic acid esters which are valuable intermediates in the manufacture of, or are in themselves, insecticides.

The only known procedure for the preparation of compounds having the general formula:

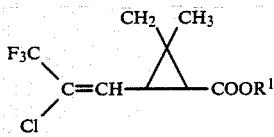

wherein $R^1$ is a lower alkyl group, from compounds having the general formula:

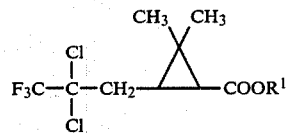

has been dehydrohalogenation using 1,5-diazabicyclo[5,4,0]undec-5-ene (DBU) as the dehydrohalogenation agent. DBU is an expensive compound, and it was therefore desirable to find a cheaper alternative.

According to the present invention there is provided a process for the preparation of a compound having the general formula:

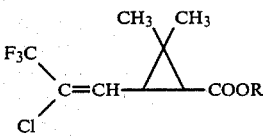

wherein R is a lower alkyl, m-phenoxybenzyl, α-cyano-m-phenoxybenzyl or α-ethynyl-m-phenoxybenzyl group, which comprises reacting a compound having the general formula:

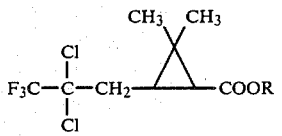

wherein R has the meaning stated above, with an alkali metal carbonate in a polar aprotic solvent. In this specification "lower alkyl group" means an alkyl group containing from 1 to 4 carbon atoms.

Examples of the alkali metal carbonates which may be used are lithium carbonate, potassium carbonate and, because of its cheapness and ready availability, sodium carbonate.

Examples of the polar aprotic solvents which may be used are hexamethylphosphoramide, diethylformamide, dimethylformamide and dimethylacetamide.

The amount of alkali metal carbonate which is used may be from 1 to 20 moles, preferably 1 to 5 moles, per mole of the compound of formula (II).

The amount of polar aprotic solvent which is used may be from 3 to 200 moles, preferably 5 to 20 moles per mole of the compound of formula (II).

The reaction may be carried out at a temperature from 50° to 250° C., under superatmospheric pressure if necessary, conveniently from 100° to 200° C., for a reaction time of several minutes to several hours.

The progress of the reaction can be followed by analytical sampling of the reaction mixture, for example, by gas-liquid chromatographic (GLC) analysis.

Isolation of the reaction product is carried out by conventional means. For example, the product may be precipitated from solution in the polar aprotic solvent by addition of another solvent which is miscible with the polar aprotic solvent but in which the reaction product of formula (I) is insoluble. A suitable solvent for this purpose is water. The precipitated product may then be extracted from the aqueous mixture with an organic solvent, for example, dichloromethane, followed by removal of the organic solvent, if desired under reduced pressure, to give the product of formula (I).

Compounds of formula (I, R=H or lower alkyl) are useful as intermediates in the preparation of insecticides or, when R is m-phenoxybenzyl, α-cyano-m-phenoxybenzyl or α-ethynyl-m-phenoxybenzyl, are themselves insecticides. For example, the compound (I, R=m-phenoxybenzyl) which is a potent insecticide, can be prepared by transesterification of (I, R=lower alkyl) with m-phenoxybenzyl alcohol, by a method analogous to that described in our German Offenlegungsschrift No. 2716772. The invention is illustrated by the following Examples.

EXAMPLE 1

A mixture of ethyl 3-(2',2'-dichloro-3',3',3'-trifluoropropyl)-2,2-dimethylcyclopropane-1-carboxylate (II, R=ethyl) (5.0 g), anhydrous sodium carbonate (5.0 g) and dimethylacetamide (20 ml) is stirred under an atmosphere of nitrogen and heated at 145°–150° C. (internal temperature) for 3 hours.

The reaction mixture is cooled to room temperature, diluted with dichloromethane and filtered. The filtrate is extracted with water, dried over anhydrous sodium sulphate and the solvent is removed by evaporation under reduced pressure to afford a substantially pure sample of ethyl 3-(2'-chloro-3',3',3'-trifluoropropenyl)-2,2-dimethylcyclopropane-1-carboxylate (I, R=ethyl). The product was identified by comparison of its $^1$Hnmr and infra-red spectra with those of an authentic sample.

EXAMPLE 2

A mixture of ethyl 3-(2',2'-dichloro-3',3',3'-trifluoropropyl)-2,2-dimethylcyclopropane-1-carboxylate (31 g.), anhydrous sodium carbonate (10.6 g.) and dimethylacetamide (100 ml) is stirred under an atmosphere of nitrogen and heated at 130°–140° C. for 48 hours. GLC analysis then showed the reaction to be substantially complete.

The reaction mixture is cooled to room temperature, poured into water and extracted with dichloromethane. The dichloromethane extract is washed with dilute acid, then with water, dried and concentrated under reduced pressure to yield crude ethyl 3-(2'-chloro-3',3',3'-trifluoropropenyl)-2,2-dimethylcyclopropane-1-carboxylate as a dark oil. Yield 21.6 g. $^{19}$F nmr analysis showed the product to contain approximately 20% by weight of the corresponding acetylenic compound, ethyl 3-(3',3',3'-trifluoropropynyl)-2,2-dimethylcyclopropane-1-carboxylate, which can be readily removed by distillation of the crude material.

EXAMPLE 3

The procedure described in Example 2 is repeated except that the 10.6 g. of anhydrous sodium carbonate are replaced by 13.8 g. of anhydrous potassium carbonate, the reaction being carried out at 140° C. for 13 hours. GLC analysis then showed the reaction to be complete. The yield of crude product is 30.4 g. and $^{19}$F nmr analysis showed it to contain approximately 18% by weight of the corresponding acetylenic derivative.

EXAMPLE 4

Ethyl 3-(2',2'-dichloro-3',3',3'-trifluoropropyl)-2,2-dimethylcyclopropane-1-carboxylate (15.35 Kg) and anhydrous potassium carbonate (6.9 Kg) were charged in turn into dimethylacetamide (46 l.), and the stirred suspension was heated at 138°–146° for 9.5 hours. The batch was cooled to room temperature, discharged into water (130 l.) and then extracted with dichloromethane (30 l.). The dichloromethane solution was washed with 3% w/w aqueous hydrochloric acid (2×30 l.) and then with 10% w/w brine (2×30 l.), and finally concentrated under reduced pressure to afford the crude product (12.65 Kg). The latter was distilled and ethyl 3-(2'-chloro-3',3',3'-trifluoropropenyl)-2,2-dimethylcyclopropane-1-carboxylate (3.12 Kg) was collected at b.p. 79°–89° C./2.0–2.5 mm Hg. pressure. The fore-runnings were redistilled and a further quantity (4.39 Kg) of product was obtained having b.p. 62°–70° C./0.75–0.90 mm Hg. pressure. The total yield was 7.5 Kg. The product in the combined distillates had a cis/trans ratio of approximately 70/30. A further fraction from the second distillation (b.p. 65°–70° C./0.8 mm Hg. pressure) was rich in trans-isomer and was retained separately.

I claim:

1. A process for the preparation of a cyclopropane carboxylic acid ester having the general formula:

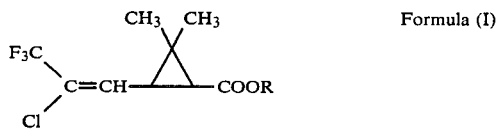

Formula (I)

wherein R is a lower alkyl, m-phenoxybenzyl, α-cyano-m-phenoxybenzyl or α-ethynyl-m-phenoxybenzyl group, which comprises reacting a compound having the general formula:

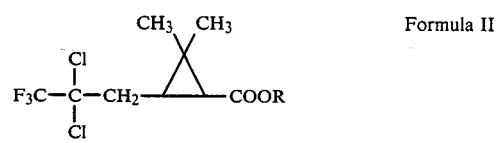

Formula II wherein R has the meanings stated above, with an alkali metal carbonate in a polar aprotic solvent, the alkali metal carbonate being selected from the group consisting of sodium carbonate and potassium carbonate.

2. A process as claimed in claim 1 wherein the amount of alkali metal carbonate which is used is from 1 to 20 mols per mol of the compound of formula (II).

3. A process as claimed in claim 1 wherein the amount of alkali metal carbonate which is used is from 1 to 5 mols per mol of the compound of formula (II).

4. A process as claimed in claim 1 wherein the amount of polar aprotic solvent which is used is from 3 to 200 mols per mol of the compound of formula (II).

5. A process as claimed in claim 1 wherein the amount of polar aprotic solvent which is used is from 5 to 20 mols per mol of the compound of formula (II).

6. A process as claimed in claim 1 wherein the reaction temperature is from 50° to 250° C.

7. A process as claimed in claim 1 wherein the reaction temperature is from 100° to 200° C.

* * * * *